United States Patent
Wada et al.

(10) Patent No.: US 10,244,942 B2
(45) Date of Patent: Apr. 2, 2019

(54) OPHTHALMOLOGIC PHOTOGRAPHING APPARATUS, METHOD, AND STORAGE MEDIUM

(71) Applicant: CANON KABUSHIKI KAISHA, Tokyo (JP)

(72) Inventors: Etsuro Wada, Yokohama (JP); Hiroki Uchida, Tokyo (JP)

(73) Assignee: Canon Kabushiki Kaisha, Tokyo (JP)

(*) Notice: Subject to any disclaimer, the term of this patent is extended or adjusted under 35 U.S.C. 154(b) by 0 days.

(21) Appl. No.: 15/450,980

(22) Filed: Mar. 6, 2017

(65) Prior Publication Data
US 2017/0258327 A1 Sep. 14, 2017

(30) Foreign Application Priority Data
Mar. 10, 2016 (JP) .................... 2016-047309

(51) Int. Cl.
| A61B 3/15 | (2006.01) |
| A61B 3/00 | (2006.01) |
| A61B 3/10 | (2006.01) |
| A61B 3/113 | (2006.01) |

(52) U.S. Cl.
CPC ............ *A61B 3/152* (2013.01); *A61B 3/0025* (2013.01); *A61B 3/0041* (2013.01); *A61B 3/102* (2013.01); *A61B 3/113* (2013.01)

(58) Field of Classification Search
CPC ........... A61B 3/152; A61B 3/14; A61B 3/102; A61B 3/12; A61B 3/0025
USPC ........................................... 351/208
See application file for complete search history.

(56) References Cited

U.S. PATENT DOCUMENTS
2013/0194543 A1* 8/2013 Iwase .................... A61B 3/102 351/206
2013/0258286 A1* 10/2013 Iwase .................. A61B 3/0041 351/208

FOREIGN PATENT DOCUMENTS
JP 2008-289642 A 12/2008

* cited by examiner

*Primary Examiner* — Mohammed A Hasan
(74) *Attorney, Agent, or Firm* — Canon U.S.A., Inc. IP Division

(57) ABSTRACT

An ophthalmologic photographing apparatus includes
a determination unit configured to determine, using the detected information, whether or not an imaging area for imaging an eye is beyond an edge of a predetermined range of movement of the eye to be examined, and
a tracking control unit configured to track the imaging area using the detected information, in a case where an imaging mode different from a follow-up imaging mode is selected and the imaging area is determined not to be beyond the edge, to not track the imaging area, in a case where an imaging mode different from the follow-up imaging mode is selected and the imaging area is determined to be beyond the edge, and to track, using the detected information, the imaging area without making the determination by the determination unit, in a case where the follow-up imaging mode is selected.

21 Claims, 13 Drawing Sheets

OPHTHALMOLOGIC PHOTOGRAPHING APPARATUS, METHOD, AND STORAGE MEDIUM

BACKGROUND

Field of the Disclosure

The present disclosure relates to an ophthalmologic photographing apparatus that images an eye to be examined.

Description of the Related Art

In recent years, eye examination is drawing attention since it is effective for early diagnosis of lifestyle diseases and various diseases with high rankings among causes of blindness. Most of all, ophthalmic tomogram acquisition apparatuses such as fundus cameras and optical coherence tomography (OCT: Optical Coherence Tomography), which are used at eye clinics and the like, can quantify the state of a disease. Hence, these apparatuses are expected to be useful to more accurately diagnose diseases. With a general OCT, a photographer determines imaging parameters (for example, a target region, an imaging range, the level of detail, and a scanning method) of a cross-sectional image, and then captures a cross-sectional image of a local region of an eye on the basis of the imaging parameters. Moreover, an ophthalmologic photographing apparatus is known which accepts, from a user, a specification of an imaging position for a cross-sectional image on a screen where a front fundus image of a fundus camera or a scanning laser ophthalmoscope (SLO: Scanning Laser Ophthalmoscope) is displayed, and captures the cross-sectional image.

If changes in the condition of the same region of the same patient are observed such as an observation of the progress of a disease of an eye, the prescription of drugs, and post-operative follow-up, it is required to capture cross-sectional images of the same region at intervals over a long time. Furthermore, comparisons of fewer wide-area and high-definition cross-sectional images of the same region that captured a lesion are suitable for comparisons of secular changes.

Moreover, an eye moves to change the line of sight, for example, involuntary eye movement, even during fixation, it is difficult to fix the position of an eye of an examinee. Hence, it is difficult to cause the eye to stay at the same coordinates in a coordinate system of the apparatus and capture an image of the eye. Japanese Patent Laid-Open No. 2008-289642 discloses an OCT apparatus including a tracking function that determines the suitability of a fixation state of an eye to be examine while a fixation target is being presented and, if the fixation state is judged to be inappropriate, corrects the position of an imaging area being a position for acquiring a tomographic image on the basis of the displacement of the eye to be examined.

SUMMARY

One embodiment of an ophthalmologic photographing apparatus according to the present disclosure may include:

a detection unit configured to detect information on movement of an eye to be examined;

a selection unit configured to select one of a plurality of imaging modes including at least a follow-up imaging mode;

a determination unit configured to determine, using the detected information, whether or not an imaging area for imaging the eye to be examined is beyond an edge of a predetermined range; and a tracking control unit configured (a) to track the imaging area using the detected information, in a case where an imaging mode different from the follow-up imaging mode is selected and the imaging area is determined not to be beyond the edge of the predetermined range, (b) to not track the imaging area, in a case where an imaging mode different from the follow-up imaging mode is selected and the imaging area is determined to be beyond the edge of the predetermined range, and (c) to track, using the detected information, the imaging area without making the determination by the determination unit, in a case where the follow-up imaging mode is selected.

Further features of the present disclosure will become apparent from the following description of exemplary embodiments (with reference to the attached drawings).

DESCRIPTION OF THE EMBODIMENTS

An ophthalmologic photographing apparatus such as an OCT apparatus has a function of changing the position of an imaging area to track the movement of an eye to be examined and achieving the imaging of the same region even if the eye to be examined moves during imaging. There is generally a limitation on a range where the imaging area can track the movement of the eye to be examined. This is because the ophthalmologic photographing apparatus has an imaging guarantee range that is determined by optical design as in another optical apparatus. In other words, when the imaging area moves out from the imaging guarantee range due to the movement of the eye to be examined during the imaging of the eye to be examined, the quality of an image of the eye to be examined may be reduced. Hence, it is preferable to set the range where the imaging area can track the movement of the eye to be examined to be within the imaging guarantee range.

However, even if the imaging range lies off the edge of the imaging guarantee range, it may be desired to image the eye to be examined knowing that the quality of the image of the eye to be examined is reduced, depending on the circumstance such as for the purpose of a diagnosis. For example, let's consider a case of follow-up imaging (the imaging of a current image of the same region as a past image for the purpose of a follow-up). At this point in time, there is a case where some patients cannot fixate the eye steadily, and accordingly, an image is always captured when the imaging area is located off the edge of the imaging guarantee range even if the above-mentioned tracking is performed. Such a case results in capturing an image at a position where the imaging area lies off the edge of the imaging guarantee range in past imaging. In this case, at the time of current imaging, the imaging of the same region as the past imaging is required even if the quality of the image of the eye to be examined is reduced.

An object of the embodiments of the present disclosure is considering such a problem and having a configuration where a suitable image of an eye to be examined can be acquired in accordance with the circumstance such as for the purpose of diagnosis (for example, follow-up imaging). Exemplary embodiments of the present disclosure are described in detail with reference to the drawings.

First Exemplary Embodiment (Main Body Configuration)

Figure 1:
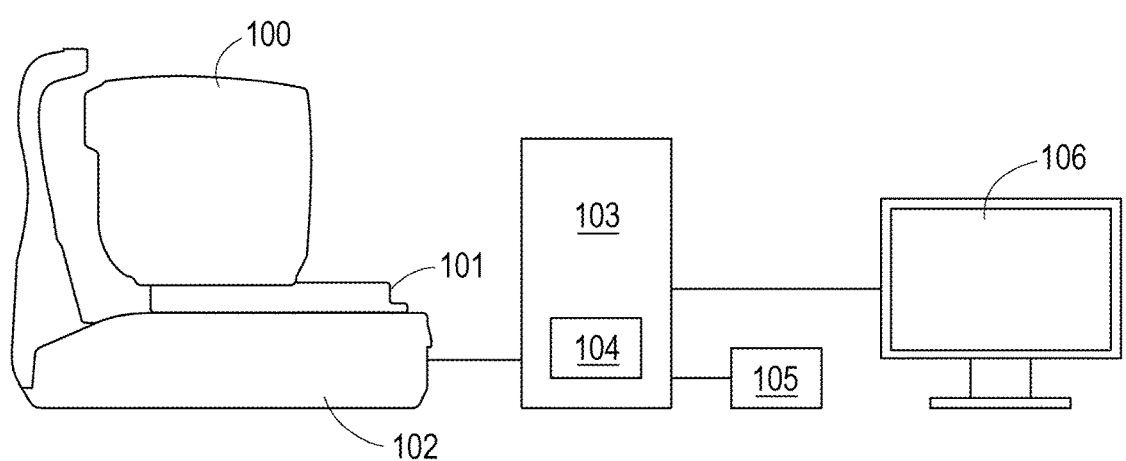
FIG. 1 is an overall configuration diagram of first to fourth exemplary embodiments of the subject disclosure.

FIG. 1 is a side view of an optical coherence tomography apparatus (an example of the ophthalmologic photographing apparatus) in a first exemplary embodiment. Firstly, a measuring optical system 100 acquires an anterior eye portion image, and an SLO fundus image and a tomographic image of an eye to be examined. In other words, optical systems for acquiring them are partially shared. Moreover, a stage unit 101 can move the measuring optical system 100 backward, forward, left, and right. Moreover, a base unit 102 includes a spectrometer described below. Moreover, a computer 103 controls the stage unit, controls alignment operations, configures a tomographic image, and the like. A storage unit 104 stores a program for tomographic imaging, patient information, imaging data, statistic information of a normal database, and the like. Moreover, an input unit 105 provides instructions to the computer and, specifically, includes a keyboard and a mouse. A display unit 106 is, for example, a monitor. The computer 103 is also an example of a display control unit to display, for example, an image of the eye to be examined on the display unit 106.

Figure 2:
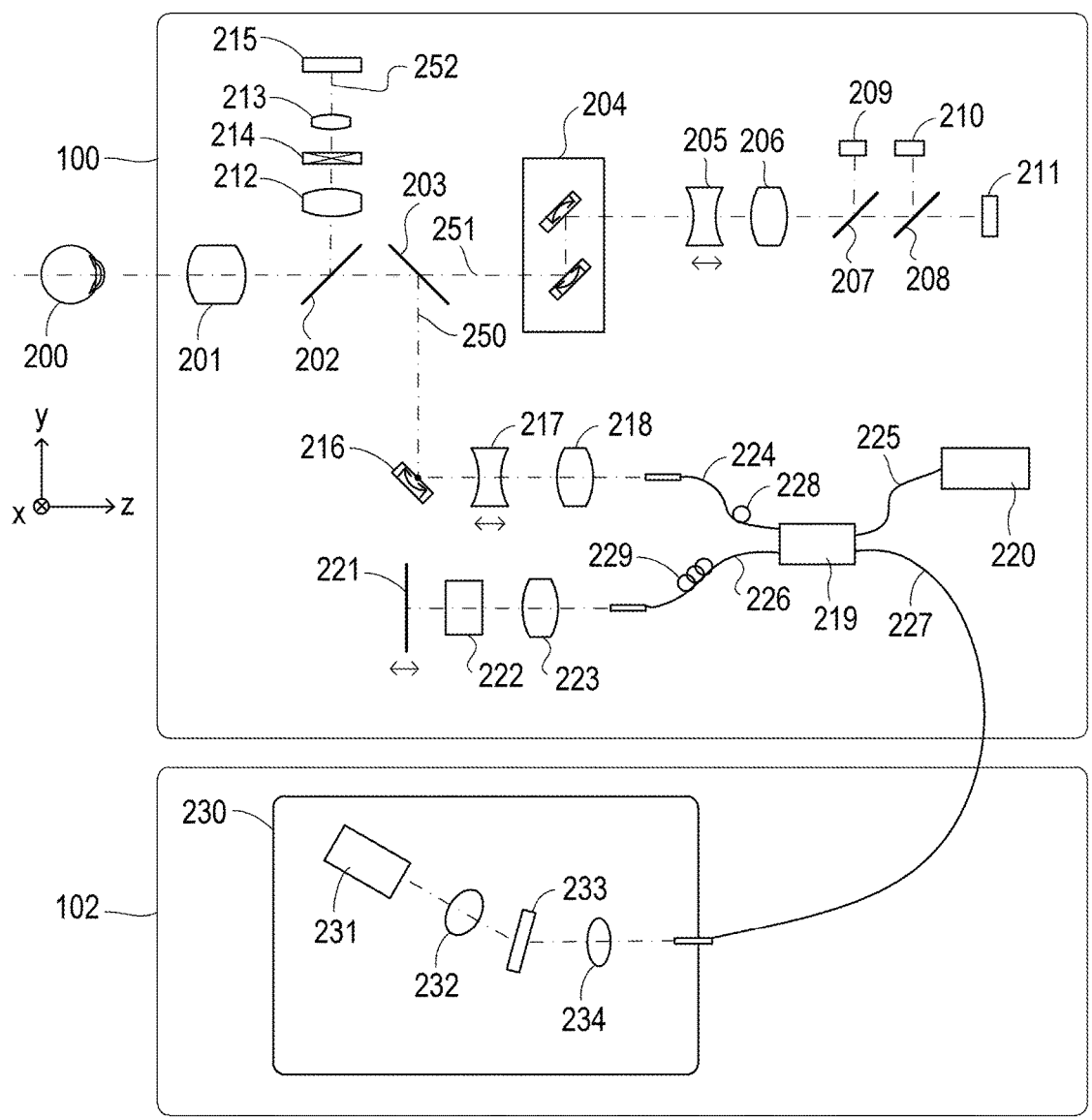
FIG. 2 is a diagram for describing a measuring optical system of the first to fourth exemplary embodiments of the subject disclosure.

Next, the configurations of the measuring optical system and the spectrometer of the first exemplary embodiment are described with reference to FIG. 2. Firstly, the inside of the measuring optical system 100 is described. An objective lens 201 is placed facing an eye to be examined 200. A first dichroic mirror 202 and a second dichroic mirror 203 are placed on an optical axis of the objective lens 201. These dichroic mirrors branch light to an optical path 250 of an OCT optical system, an optical path 251 for an SLO optical system and a fixation lamp, which serves for both observation of the eye to be examined and acquisition of an SLO fundus image, and an optical path 252 for observation of the anterior eye portion, according to the wavelength bands. Moreover, the optical path 251 for the SLO optical system and the fixation lamp includes an SLO scanning unit 204, lenses 205 and 206, a mirror 207, a third dichroic mirror 208, a photodiode 209, an SLO light source 210, and a fixation lamp 211. Moreover, the mirror 207 is a prism onto which a perforated mirror or hollow mirror has been evaporated, and separates illumination light from the SLO light source 210 and return light from the eye to be examined. The third dichroic mirror 208 separates light into the optical paths to the SLO light source 210 and the fixation lamp 211, according to the wavelength bands.

Moreover, the SLO scanning unit 204 scans the eye to be examined 200 with light emitted from the SLO light source 210 and the fixation lamp 211, and includes an X scanner that scans in an X-direction, and a Y scanner that scans in a Y-direction. In the exemplary embodiment, the X scanner requires fast scanning and accordingly includes a polygonal mirror, whereas the Y scanner includes a galvanometer mirror. Moreover, the lens 205 is driven by an unillustrated motor to cause the SLO optical system and the fixation lamp to come into a focus. The SLO light source 210 produces light of a wavelength of approximately 780 nm. The photodiode 209 detects the return light from the eye to be examined. The fixation lamp 211 produces visible light to encourage an examinee to fixate the eye. At this point in time, the examinee is presented the fixation lamp. Moreover, the light emitted from the SLO light source 210 is reflected from the third dichroic mirror 208, passes through the mirror 207, travels through the lenses 206 and 205, and scans the eye to be examined 200 with the SLO scanning unit 204. The return light from the eye to be examined 200 returns along the same path as projection light, and is then reflected from the mirror 207, and guided to the photodiode 209. Accordingly, an SLO fundus image being an example of a front image is obtained. The front image may be, for example, an integrated image generated from three-dimensional OCT data, a C-scan image, or an En-face image based on a segmentation (layer extraction) result, instead of the SLO fundus image. Moreover, instead of the SLO optical system, what is called a fundus camera optical system may be applied to partially share the fundus camera optical system and the OCT optical system.

Moreover, the light emitted from the fixation lamp 211 passes through the third dichroic mirror 208 and the mirror 207, travels through the lenses 206 and 205, and scans the eye to be examined 200 with the SLO scanning unit 204. At this point in time, the fixation lamp 211 is caused to blink in step with the movement of the SLO scanning unit to create an arbitrary shape at an arbitrary position on the eye to be examined 200 and encourage the examinee to fixate the eye.

Moreover, on the optical path 252 for observation of the anterior eye portion are lenses 212 and 213, a split prism 214, and a CCD 215 for observation of the anterior eye portion that detects infrared light. The CCD 215 has a sensitivity to a wavelength of unillustrated irradiation light for observation of the anterior eye portion, specifically, around 970 nm. The split prism 214 is placed at a position conjugated with the pupil of the eye to be examined 200, and can detect a distance to the eye to be examined 200 in a Z-direction (the front-and-back direction) of the measuring optical system 100 as a split image of the anterior eye portion.

Moreover, the optical path 250 of the OCT optical system forms the OCT optical system as described above, and is for capturing a tomographic image of the eye to be examined 200. More specifically, the optical path 250 is for obtaining an interfering signal to form a tomographic image. An X-Y scanner 216 scans the eye to be examined with light. The X-Y scanner 216 is illustrated as one sheet of mirror, but is a galvanometer mirror that scans in two directions of the X- and Y-directions. Moreover, there are lenses 217 and 218. Of them, the lens 217 is driven by an unillustrated motor to cause the light from an OCT light source 220 emitted from a fiber 224 connected to an optical coupler 219 to come into focus on the eye to be examined 200. The focusing causes the return light from the eye to be examined 200 to simultaneously form a spot-like image and be incident on a tip of the fiber 224.

Next, the configurations of the optical path from the OCT light source 220, a reference optical system, and the spectrometer are described. There are the OCT light source 220, a reference mirror 221, a dispersion compensation glass 222, a lens 223, the optical coupler 219, single-mode optical fibers 224 to 227 integrated by being connected to the optical coupler, and a spectrometer 230. These configurations form a Michelson interference system. The light emitted from the OCT light source 220 travels along the optical fiber 225 and is split into measurement light on the optical fiber 224 side and reference light on the optical fiber 226 side through the optical coupler 219. The measurement light is applied to the eye to be examined 200 being an observation target through the above-mentioned OCT optical system optical path, and reaches the optical coupler 219 along the same optical path due to reflection and scattering by the eye to be examined.

On the other hand, the reference light reaches the reference mirror 221 through the optical fiber 226, the lens 223, and the dispersion compensation glass 222 that has been inserted to adjust the dispersion of the measurement light and the reference light, and is reflected from the reference mirror 221. The reference light returns along the same optical path and reaches the optical coupler 219. The optical coupler 219 multiplexes the measurement light and the reference light into interference light. When the optical path length of the measurement light and the optical path length of the reference light become equal, interference occurs. The reference mirror 221 is held by an unillustrated motor and driving mechanism in such a manner as to be adjustable in the optical axis direction. The reference mirror 221 can adjust the optical path length of the reference light to the optical path length of the measurement light, which changes depending on the eye to be examined 200. The interference light is guided to the spectrometer 230 through the optical fiber 227.

Moreover, a polarization adjustment unit 228 is provided in the optical fiber 224 on the measurement light side. A polarization adjustment unit 229 is provided in the optical fiber 226 on the reference light side. These polarization adjustment units have some portions where the optical fiber is routed in a loop form. The loop portion is rotated about a longitudinal direction of the fiber to add a twist to the fiber. Therefore, the polarized states of the measurement light and the reference light can be adjusted to agree with each other.

Moreover, the spectrometer 230 includes lenses 232 and 234, a diffraction grating 233, and a line sensor 231. The interference light emitted from the optical fiber 227 is collimated through the lens 234, and is then dispersed by the diffraction grating 233, and forms an image on the line sensor 231 by the lens 232.

Next, the peripheral of the OCT light source 220 is described. The OCT light source 220 is an SLD (Super Luminescent Diode) being a representative low-coherent light source. Its central wavelength is 855 nm, and wavelength bandwidth is approximately 100 nm. Here, the bandwidth is an important parameter since it influences the resolution in the optical axis direction of a tomographic image obtained. In terms of the type of the light source, the SLD is selected here. However, it is simply required to be capable of emitting low-coherent light. For example, an ASE (Amplified Spontaneous Emission) can be used. In terms of the central wavelength, near infrared light is suitable considering the measurement of an eye. Moreover, the central wavelength is desired to be as short a wavelength as possible since it influences the resolution in the horizontal direction of a tomographic image obtained. From both reasons, the central wavelength is set at 855 nm. In one exemplary embodiment, the Michelson interference system is used as the interference system. However, a Mach-Zehnder interference system may be used. It is desired to use the interference system in accordance with a difference in light quantity between the measurement light and the reference light, for example, a Mach-Zehnder interference system when the difference in light quantity is large, and a Michelson interference system when the difference in light quantity is relatively small. Reconstruction processing such as a Fourier transform is performed on imaging data obtained with the above configuration; accordingly, a tomographic image of the eye to be examined can be acquired.

(OCT Examination)

Figure 3:
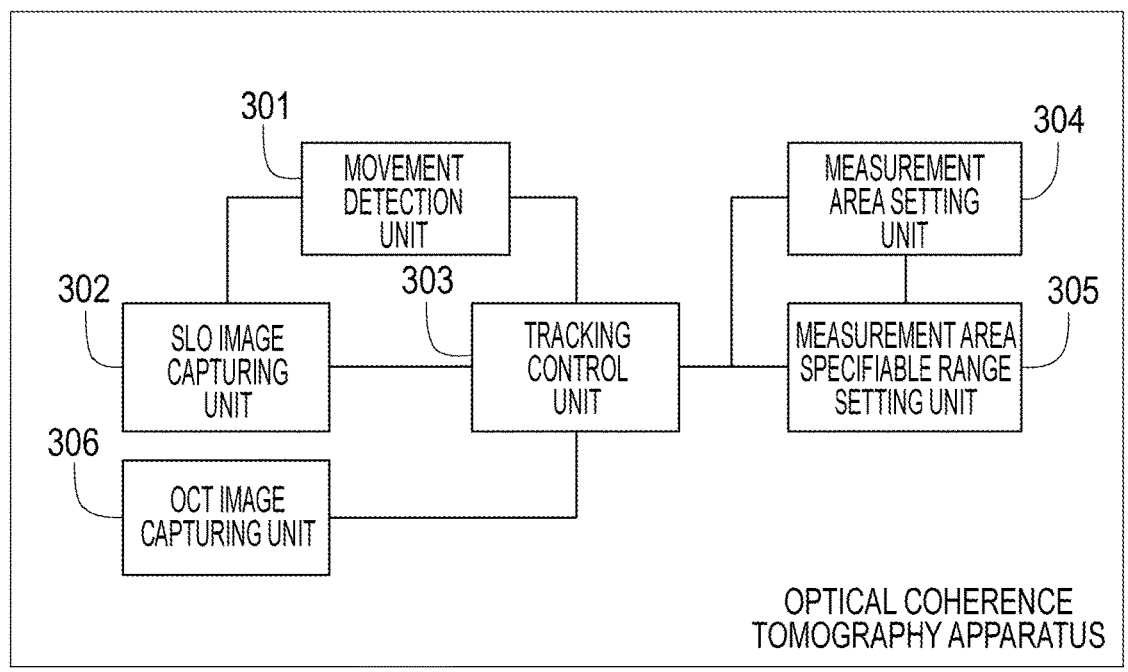
FIG. 3 is a control block diagram of the first embodiment of the subject disclosure.

Next, a control block configuration in the first exemplary embodiment is described with reference to FIG. 3. Firstly, a movement detection unit 301 detects the movement of the eye to be examined on the basis of information of an SLO image capturing unit 302, and notifies it to a tracking control unit 303. Moreover, a measurement area setting unit 304 accepts a measurement area setting instruction from an operator and, if it is within a range of a measurement area that can be specified, notifies it to the tracking control unit 303. Moreover, a measurement area specifiable range setting unit 305 sets a range where the measurement area can be specified (a trackable range), and notifies it to the tracking control unit 303. Moreover, the tracking control unit 303 controls an OCT image capturing unit 306 in such a manner as to track the movement of the eye to be examined on the basis of the results of the movement detection unit 301 and the measurement area setting unit 304. The movement detection unit 301 can be anything as long as it can detect information on the movement of the eye to be examined. There is, for example, a method that directly detects the moving amount and moving direction of the eye to be examined using a feature extracted from an image of the eye to be examined. Moreover, it may be a method that indirectly detects the moving amount and moving direction of the eye to be examined by detecting the moving amount and moving direction of the apparatus. In this case, for example, to which position a fixed ROI in an image of the eye to be examined has moved is detected. The former is an example of a method that obtains one relative position from two detection results. The latter is an example of a method that obtains one detection result as one relative position.

Figure 4:
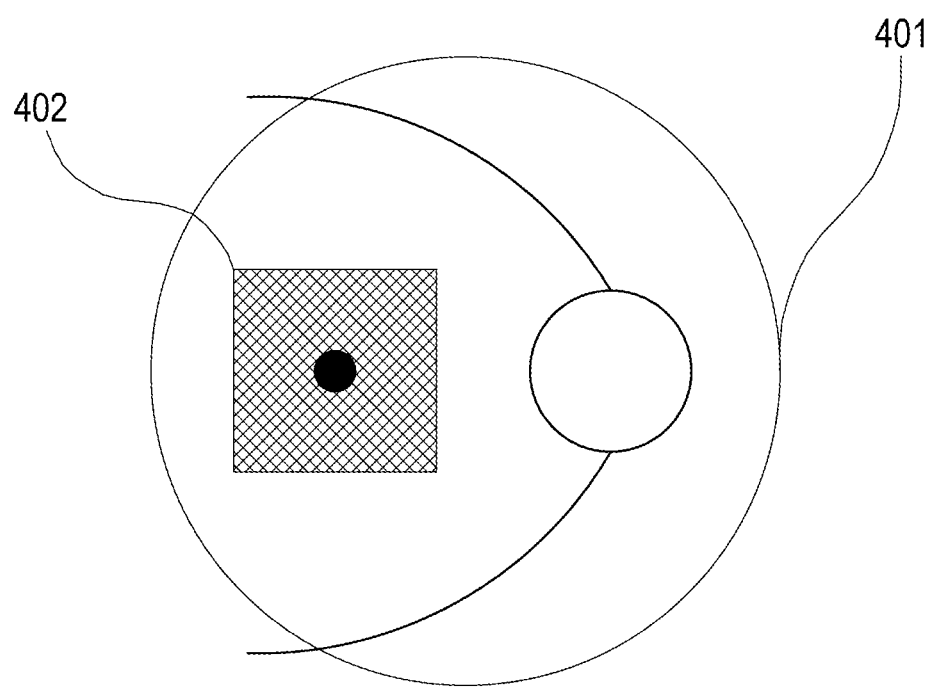
FIG. 4 is a diagram for describing general tracking operations of the subject disclosure.

Next, general tracking operations upon OCT imaging are described with reference to FIG. 4. In FIG. 4, the imaging can be performed without a reduction in the quality of an image determined by the optical properties (such as optical design) of an optical system in an imaging guarantee range 401. In other words, the imaging guarantee range 401 meets the optical properties of the optical system. An image is captured in reality in a measurement area (imaging area) 402 upon imaging. If the measurement area 402 is set outside the imaging guarantee range 401, the quality of the image is reduced. Therefore, the measurement area 402 may be able to be specified only within the imaging guarantee range 401. In this case, the tracking control unit can, for example, be configured to stop the tracking of the measurement area 402 and resume the tracking when the measurement area 402 returns again to within the imaging guarantee range 401 if the measurement area 402 moves out of the imaging guarantee range 401.

Figure 5:
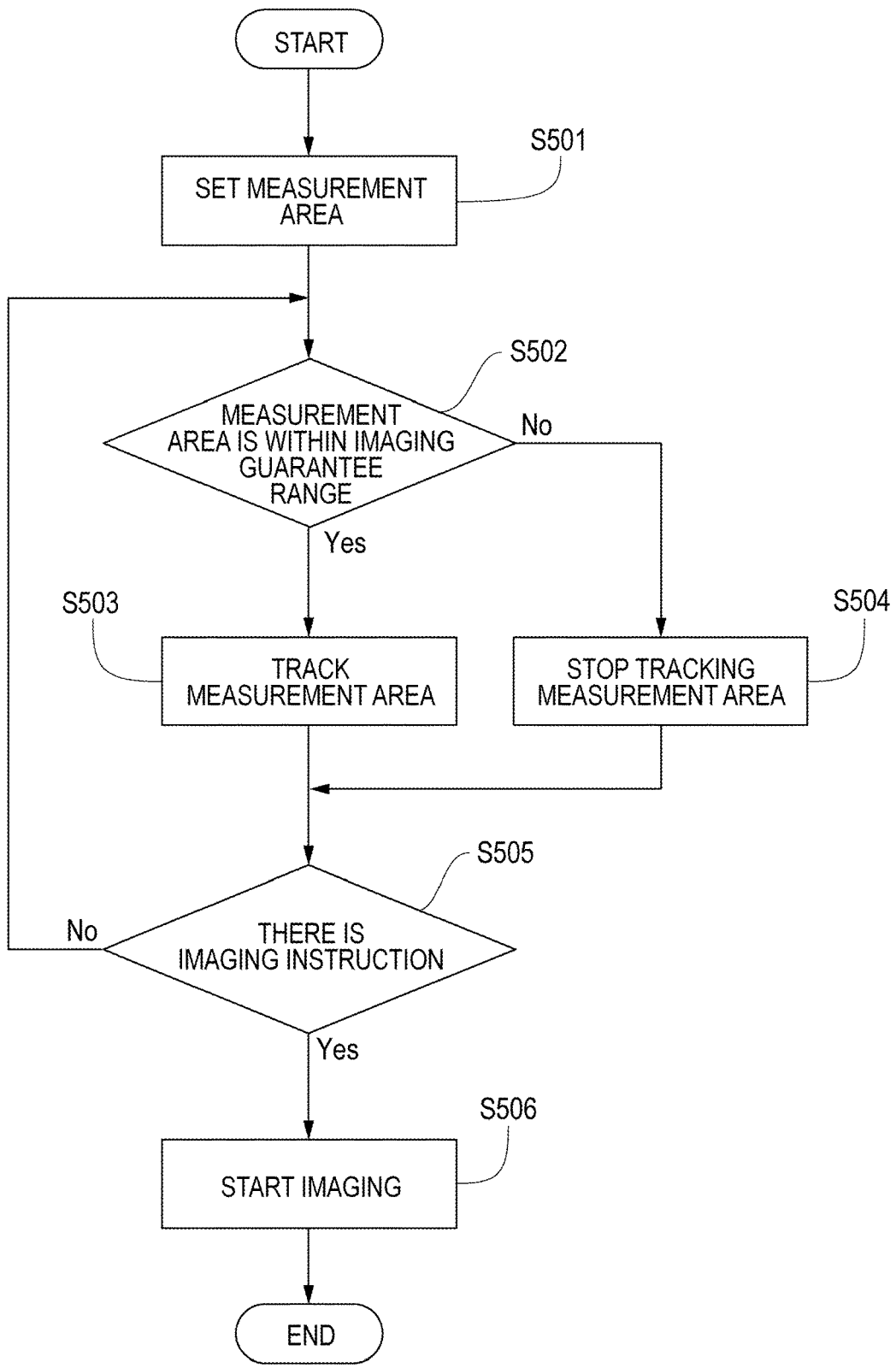
FIG. 5 is a flowchart of the general tracking operations of the subject disclosure.

The flow of processes at this point in time is described with reference to a flowchart of FIG. 5. In S501, the measurement area 402 is set. In S502, the measurement area 402 is determined whether or not to be within the imaging guarantee range 401. If the condition of S502 is satisfied, the measurement area 402 is tracked in S503. If the condition of S502 is not satisfied, the measurement area 402 is stopped being tracked in S504. In S505, whether or not there is an imaging instruction is checked. If there is an imaging instruction, imaging starts in S506. If there is no imaging instruction, the processing returns to S502 to repeat the tracking process.

Figure 6A:
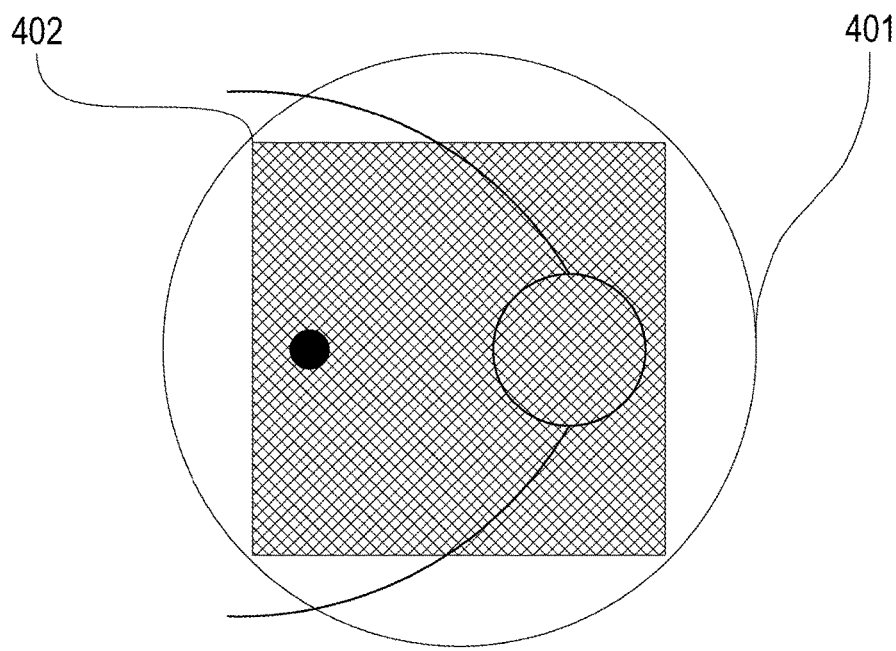
FIGS. 6A and 6B are diagrams for describing tracking control of the first exemplary embodiment of the subject disclosure.

Next, tracking control of an exemplary embodiment is described with reference to FIG. 6A, which includes the imaging guarantee range 401 and the measurement area 402. In this example, the measurement area is specified as a very large area of a shape including the optic disc and the macular area. There are hardly margins of the imaging guarantee range 401. In such a case of a wide scan, even if an examinee is not one who cannot fixate the eye steadily, even a slight movement of the eye may cause the measurement area 402 to move out from the imaging guarantee range 401. Consequently, the tracking operation stops every time the measurement area 402 moves out from the imaging guarantee range 401 so that it has been difficult to measure the same region. In the exemplary embodiment, considering such a point, control is performed such that the specifiable range of the measurement area 402 is variably changed according to the size of the measurement area 402. For example, the area of the measurement area 402 is calculated and, if the area is judged to be larger than a threshold ("Tha"), the measurement area specifiable range is extended. Upon the extension, the measurement area specifiable range may be extended in accordance with the calculated area, or may be extended to the limit where the determination of tracking can be made, using an SLO image. Consequently, a desired range can be imaged. Specifically, when Tha was set at 60% of the area of the imaging guarantee range, control could be preferably performed.

Figure 7:
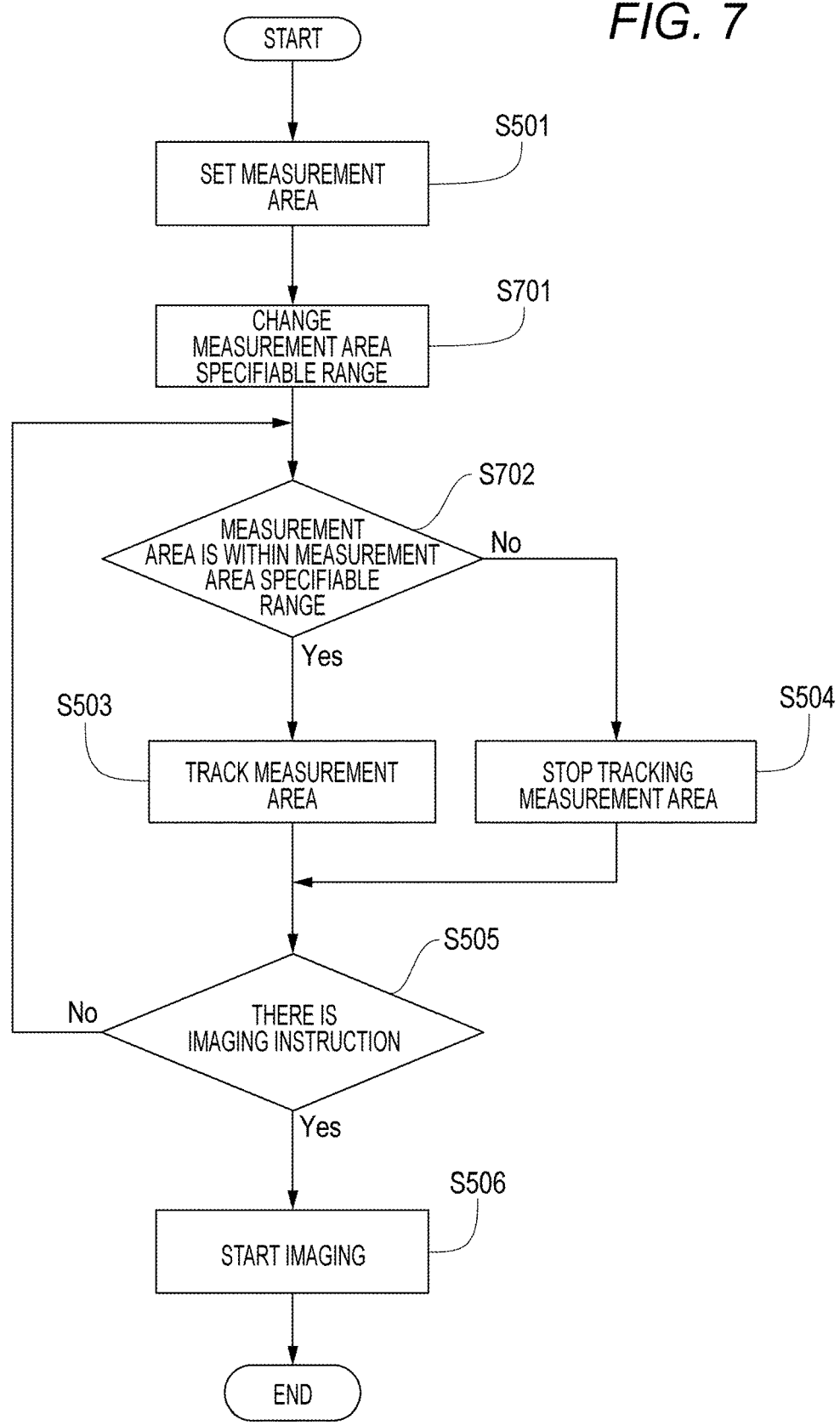
FIG. 7 is a flowchart of tracking control of the first exemplary embodiment of the subject disclosure.

A flowchart of FIG. 7 is an overview of the above flow of processes. In FIG. 7, S502 is changed from the flowchart of FIG. 5 to be set as S701 and S702. In S701, the measurement area specifiable range is changed. In S702, the subsequent processes are performed with respect to the measurement area specifiable range.

Figure 8A:
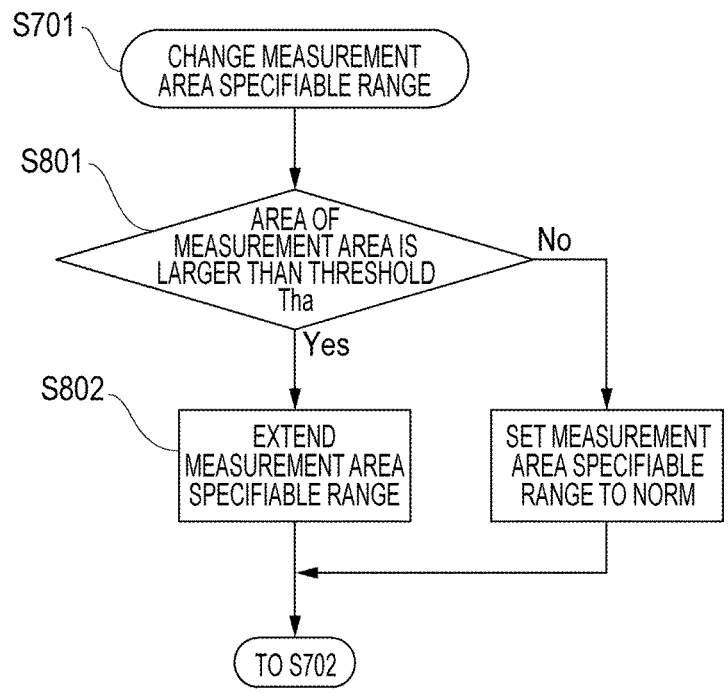
FIGS. 8A and 8B are flowcharts of tracking control of the first and second exemplary embodiments of the subject disclosure.

Furthermore, a flowchart of FIG. 8A gives a description by breaking down S701 into S801 and S802. In S801, the processing branches according to the area of the measurement area 402. In S802, the size of the measurement area specifiable range is changed.

Figure 9A:
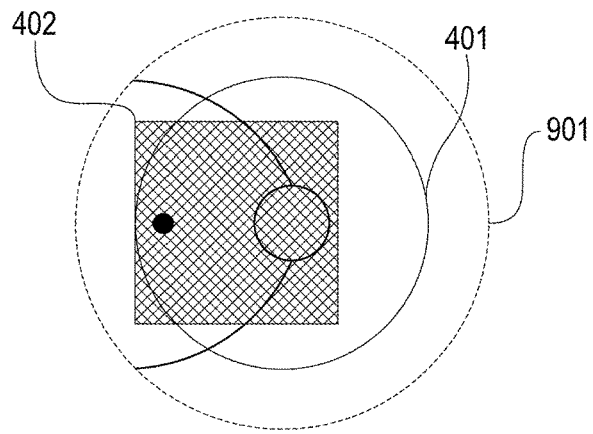
FIGS. 9A to 9C are examples where a measurement area specifiable range of the first exemplary embodiment of the subject disclosure is changed.

In an exemplary embodiment, as illustrated in FIG. 9A, a measurement area specifiable range 901 is changed to be outside the imaging guarantee range 401 on the basis of the size of the measurement area 402. In this exemplary embodiment, the imaging guarantee range 401 is circular. However, it is determined by the optical properties. Accordingly, the imaging guarantee range 401 may not be circular depending on the optical properties of the apparatus. In this case, the setting condition of the measurement area specifiable range 901 is required to be changed according to its shape.

Figure 9B:
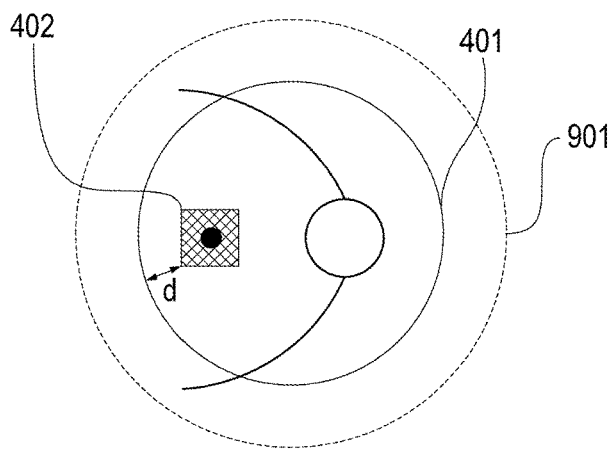

Moreover, in this exemplary embodiment, the area of the measurement area 402 is obtained. The measurement area specifiable range is then changed. However, the method is not limited to this. For example, as illustrated in FIG. 9B, a shortest distance "d" between the measurement area 402 and the imaging guarantee range 401 may be obtained to change the measurement area specifiable range 901 according to the distance. Under such control, even if the measurement area 402 is not that large area, when it is in proximity to the imaging guarantee range 401, the same region can be imaged steadily. Accordingly, it is very preferable.

Figure 9C:
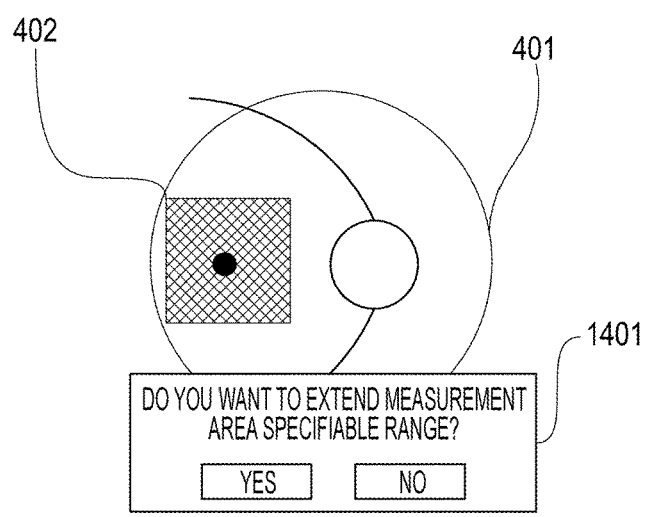

Moreover, as illustrated in FIG. 9C, if the measurement area specifiable range is changed to an area larger than the imaging guarantee range 401, a message 1401 may be issued to a user to notify the user of the necessity or unnecessity of a change in range. Moreover, if the measurement area specifiable range is changed to an area larger than the imaging guarantee range 401, it is more preferable to switch after the tracking of the normal measurement area specifiable range and a state where the tracking is not possible are repeated a predetermined number of times. Moreover, an image captured in this manner may be inferior in quality. Accordingly, it is more preferable to display information to the effect on the display unit 106 with a property of an examination image, an icon on the image, or the like.

(Radial Scan and Circle Scan)

Moreover, in this exemplary embodiment, the area of the measurement area 402 is used to change the measurement area specifiable range 901. However, the measurement area specifiable range 901 may be changed according to the shape of the measurement area 402 and a scan pattern upon imaging. Specifically, when the shape of the measurement area 402 is circular as in a radial scan, a circle scan, and the like, even if the area is the same, the possibility that the measurement area 402 lies off the edge of the imaging guarantee range 401 is reduced. In such a case, it was very preferable to, for example, extend the measurement area specifiable range when Tha increases to or above 80% of the area of the imaging guarantee range. Moreover, the boundary to extend the measurement area specifiable range 901 can be narrowed as compared to a case where the measurement area is rectangular as in a volume scan.

(Line Scan and Cross Scan)

When it is desired to give attention to one point on the eye to be examined for observation, a line scan or cross scan may be used. Generally, tracking is not performed for a volume scan. Even if the measurement area is displaced to some extent with respect to a region desired to be imaged, it may be allowed as long as the region of interest is in the volume. On the other hand, tracking is not performed for a line scan and a cross scan since a region of interest is scanned; accordingly, if the same region cannot be imaged, the imaging may be performed again.

Figure 6B:
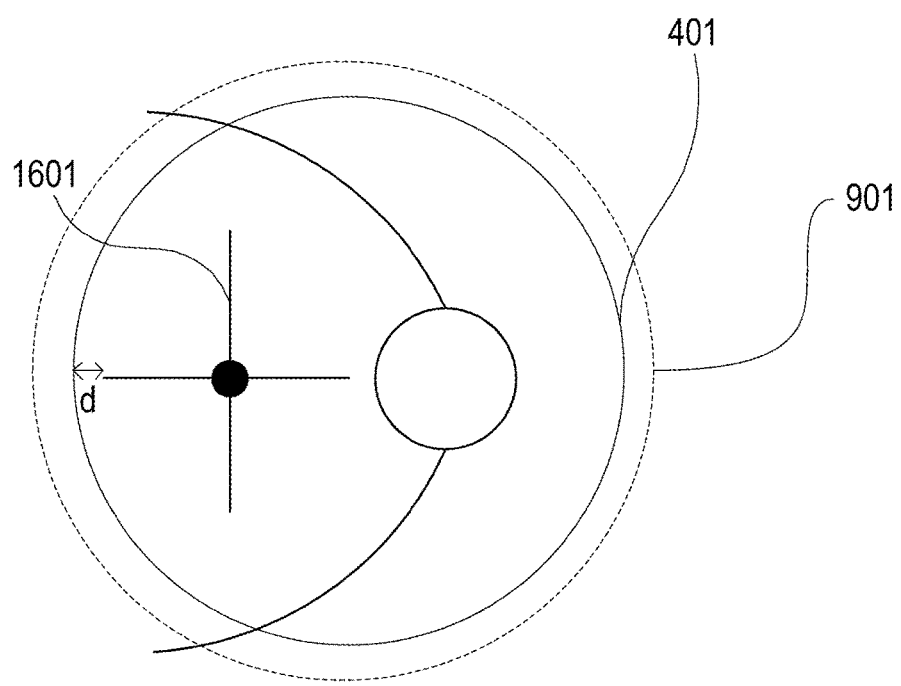

FIG. 6B is a diagram for describing a controlling method when a cross scan is performed. FIG. 6B illustrates the imaging guarantee range 401, the tracking range 901 of when the tracking range was extended, and a cross scan 1601. The cross scan 1601 corresponds to the imaging range. In the case of this scan, the shortest distance "d" between a given point on thescan and the imaging guarantee range 401 was obtained first. Next, if d was greater than a certain threshold, the tracking range was set as the imaging guarantee range as usual. Moreover, if d was greater than the certain threshold, the tracking range was controlled to be extended larger than the imaging guarantee range as in the tracking range 901. Under such control, the control could be preferably performed. As a method for calculating d, the shortest distance may be obtained from the center of a scan and the size of the scan. Moreover, as another controlling method, a minimum circle or ellipse including a scan may be obtained to perform control with a minimum value of a distance between the circle or ellipse and the imaging guarantee range 401. Moreover, in the example of FIG. 6B, the tracking range was extended evenly upward, downward, leftward, and rightward with respect to the imaging guarantee range 401. However, there is no need to stick to this. In this example, the left side of FIG. 6B has a high possibility to lying off the edge of the imaging guarantee range; accordingly, only the right side may be extended.

Second Exemplary Embodiment

Next, in a second exemplary embodiment, part of the configuration of the first exemplary embodiment is changed. A method for imaging the same location as a previous examination at the time of a follow-up examination is described. In the second exemplary embodiment, the measurement area specifiable range is made different between the time of the follow-up examination and examinations other than the follow-up examination to solve the problem. In the follow-up examination, the same location as a previous examination (an examination conducted in the past) is compared to check secular changes. Hence, imaging conditions such as a scan size and a scan mode are preferable to be the same as those at the time of the previous examination. It is important to be able to image the same location as the previous time. However, even if the settings are the same as those of the previous examination, when, for example, a scan was near the imaging guarantee range at the time of the previous examination or the fixation is unsteady, the measurement area 402 may not be within the imaging guarantee range 401. In such a case, tracking is not performed in the known controlling method. Hence, it has been difficult to image the same location as the previous time for the purpose of a follow-up. Hence, in the exemplary embodiment, even if the quality of an image is reduced to a certain extent, control is performed such that the same location as a previous examination can be imaged in a follow-up examination by setting the measurement area specifiable range 901 to be larger than that of the previous examination. The follow-up examination is also called follow-up imaging, which can be conducted by, for example, selecting a follow-up imaging mode with a selection unit (not illustrated) that selects one of a plurality of imaging modes including the follow-up imaging mode.

Firstly, at the time of the first examination, the measurement area specifiable range 901 is set to the same size as the imaging guarantee range 401. At the time of a follow-up examination, the measurement area specifiable range 901 is set to be larger than the imaging guarantee range 401 for imaging. For example, it may be set at 110% of the area of the imaging guarantee range 401, or may be extended to the limit that the determination of tracking can be made, using an SLO image. Moreover, the measurement area specifiable range 901 at the time of the first examination may be set to be smaller than the imaging guarantee range 401. For example, the area of the imaging guarantee range 401 may be calculated to set the measurement area specifiable range 901 at 70% of the imaging guarantee range 401 at the time of the first examination; accordingly, the measurement area specifiable range 901 may be extended relatively at the time of the follow-up examination.

Figure 8B:
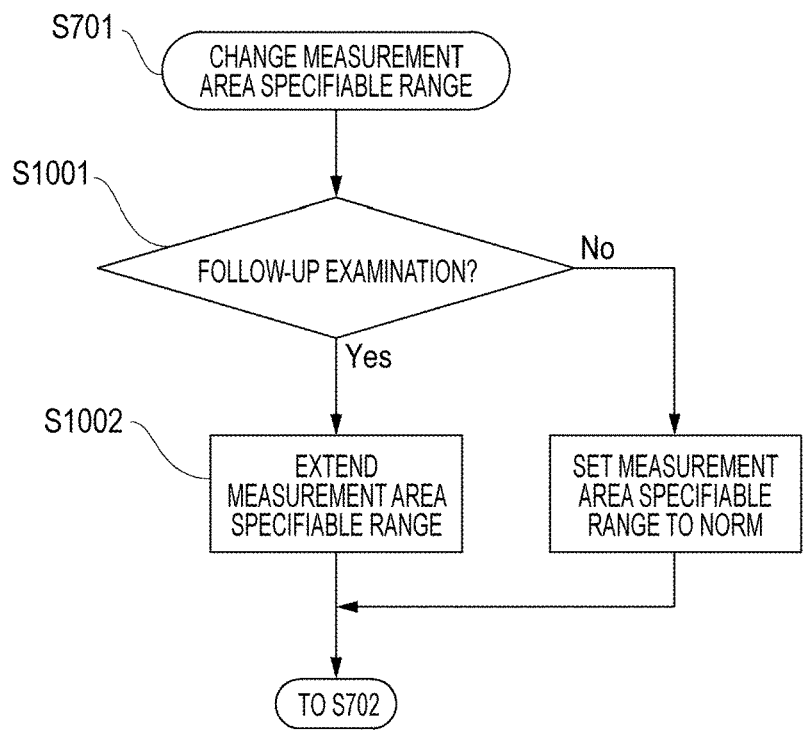

A flowchart of FIG. 8B is reflective of the above flow of processes, and is obtained by breaking down S701 of the flowchart of FIG. 7. In S1001, the processing branches according to whether or not it is a follow-up examination. In S1002, the size of the measurement area specifiable range 901 is changed. According to the method described above, even if the measurement area is not within the imaging guarantee range at the time of an OCT follow-up examination, the same location as the previous time can be imaged.

Figure 10:
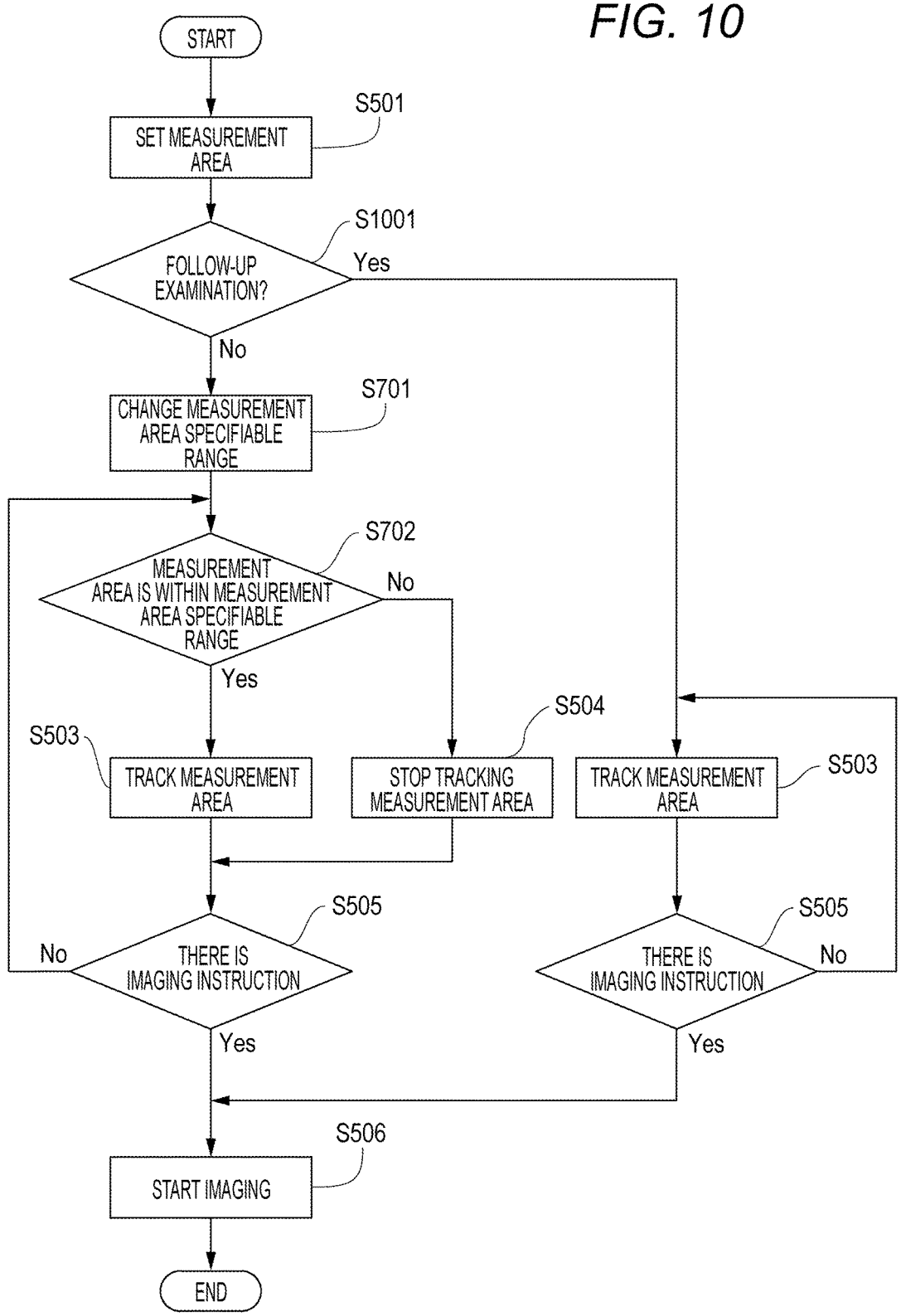
FIG. 10 is a flowchart of the second exemplary embodiment of the subject disclosure.

Moreover, in the second exemplary embodiment, the description of the tracking range of the measurement area specifiable range 901 is based on the flowchart of FIG. 8B. The embodiment is not limited to this. The processing may be performed as in, for example, a flowchart of FIG. 10. In FIG. 8B, the measurement area specifiable range 901 is extended at the time of the follow-up examination. However, the limitation on the range is not placed here. However, even if there is no such a limitation, the angle of view of an SLO image and the area required by the movement detection unit to detect the movement of the eye to be examined are still required. Accordingly, it is needless to say that there is substantially a limitation. Under such control, similar effects can be obtained. Moreover, also in the second exemplary embodiment, the message 1401 illustrated in FIG. 9C, an icon, a property, or the like, may be used to notify the extension of the tracking range.

Third Exemplary Embodiment

Figure 11:
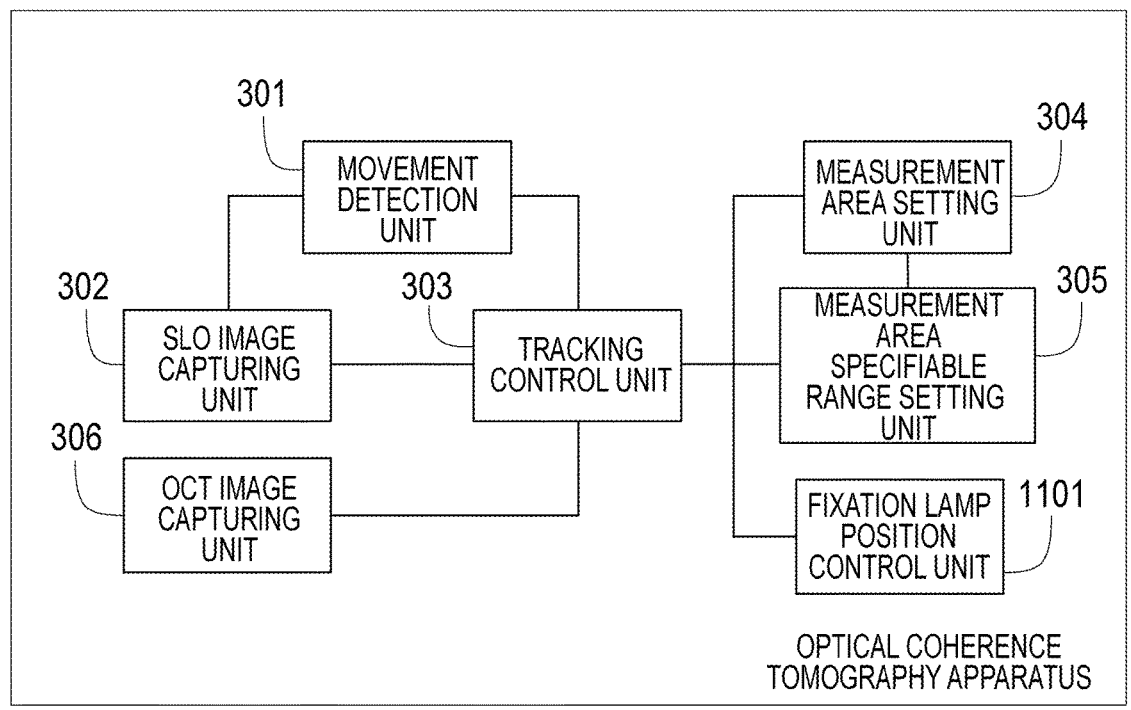
FIG. 11 is a control block diagram of the third exemplary embodiment of the subject disclosure.

Moreover, in a third exemplary embodiment, a method for solving the problem is described, changing part of the configurations of the first and second exemplary embodiments. In the third exemplary embodiment, the fixation lamp is moved to solve the problem. An apparatus configuration in the exemplary embodiment is described with reference to FIG. 11. The exemplary embodiment includes the configuration of the first exemplary embodiment, and also a fixation lamp position control unit 1101 that moves the position of the fixation lamp in response to a result of the tracking control unit 303.

Figure 12:
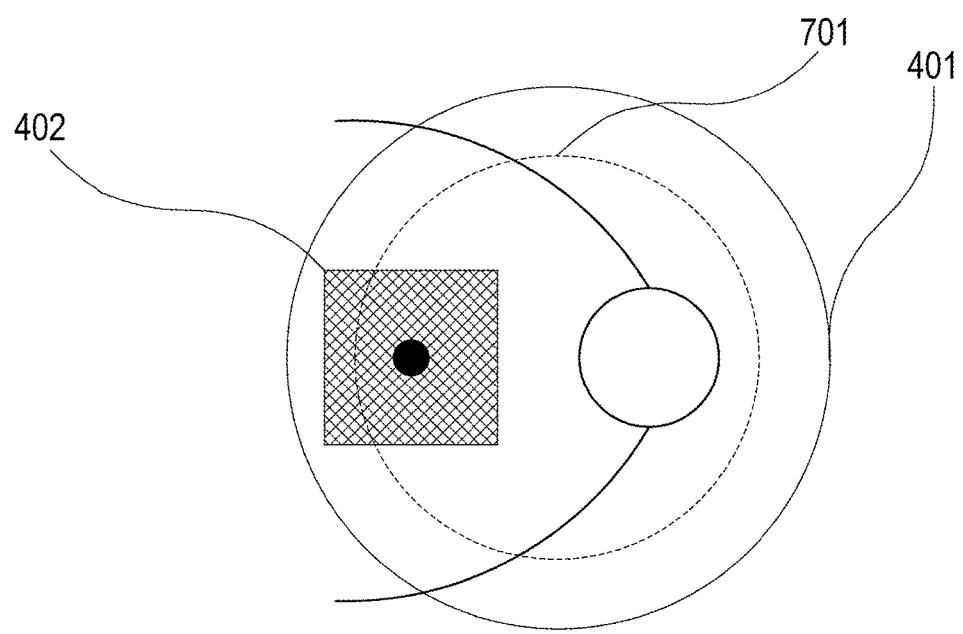
FIG. 12 is a schematic diagram of the third exemplary embodiment of the subject disclosure.

In this exemplary embodiment, the fixation lamp is moved to locate the measurement area 402 near the center of the imaging guarantee range 401 upon observation. As illustrated in FIG. 12, for example, if the measurement area 402 lies off the edge of the measurement area specifiable range 701, the fixation lamp is automatically moved. Consequently, the measurement area 402 tracks the eye to be examined and moves in such a manner as to be near the center of the imaging guarantee range 401.

Consequently, even if the fixation state of the eye to be examined changes and accordingly the measurement area 402 does not stay within the measurement area specifiable range, the fixation state of the eye to be examined is changed to allow imaging placing the measurement area 402 within the range. According to the method described above, imaging can be performed containing the measurement area in the imaging guarantee range. Furthermore, also at the time of a follow-up examination, the probability that the measurement area moves out from the imaging guarantee range can be reduced.

Fourth Exemplary Embodiment

In a fourth exemplary embodiment, the measurement area specifiable range is changed on the basis of the eye movement to solve the problem. When the eye of an examinee moves vigorously, or is not fixated well, even if the measurement area 402 is set within the imaging guarantee range 401, it may move out from the imaging guarantee range 401 during imaging. Hence, the moving amount of the eye to be examined is detected to automatically reduce the measurement area specifiable range 901. Accordingly, imaging is performed near the center of the imaging guarantee range

401. Moreover, importance is placed on being able to image a specified location during imaging. Therefore, tracking is continued beyond the imaging guarantee range 401 until the imaging is complete and, accordingly, the imaging of the specified measurement area 402 can be achieved. The measurement area specifiable range is set in advance to be small at the time of the first examination. Accordingly, at the time of a follow-up examination, the probability that the measurement area 402 moves out from the imaging guarantee range 401 due to the movement of the eye can be reduced. Therefore, it is preferable.

In such a case, it is more preferable to display a message to a user on the display unit 106 when the measurement area specifiable range is reduced. In terms of the detection of the eye movement, it is preferable to make a determination on the basis of the sum of displacement amounts of fixation for a predetermined period of time. Also in this case, the message 1401 illustrated in FIG. 9C, an icon, a property, or the like may be used to notify the change of the tracking range. According to the method described above, even if an eye of an examinee moves vigorously or is not fixated well, a specified measurement area can be imaged.

Fifth Exemplary Embodiment

Figure 13:
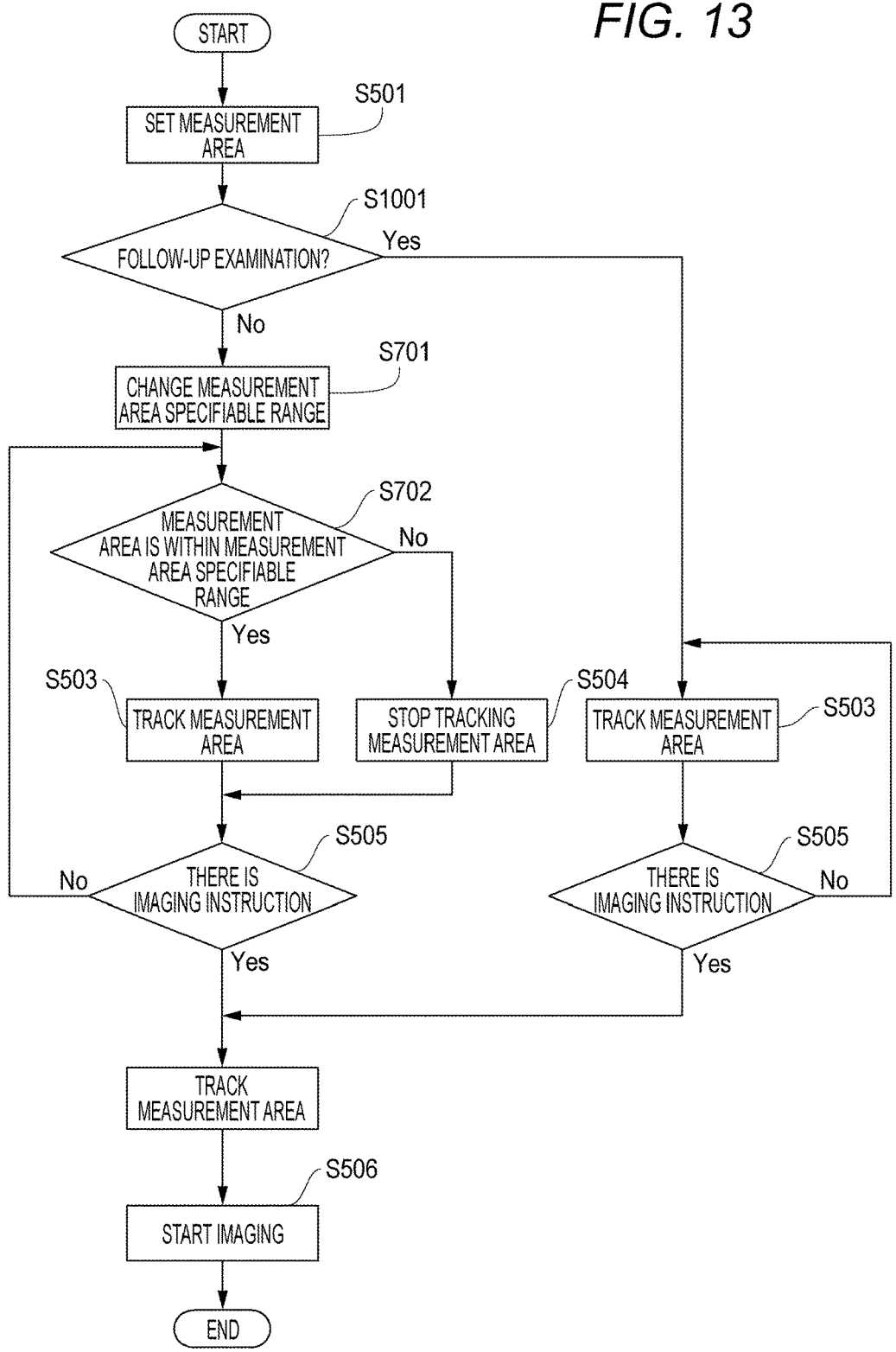
FIG. 13 is a flowchart of a fifth exemplary embodiment of the subject disclosure.

In the first exemplary embodiment, the tracking operations in the observation state being a stage before imaging in follow-up mode are described. However, operations in the imaging state are not described. When the observation state is ready and it enters the imaging state, even if the measurement area lies off the edge of the imaging guarantee range, it is preferable to be able to capture an image. FIG. 13 is a variation example of FIG. 10, and is an example where the state is always switched to the tracking state before entering the imaging state after the imaging instruction. Under such control, it is possible to image a target area even if the eye moves largely after the imaging instruction although there is a possibility to reduce the quality of the image. It is very preferable. The exemplary embodiment is described as the variation example of FIG. 10, but is not limited to this. A combination with another tracking control method described in the embodiments of the present disclosure is also feasible, which can take similar effects.

Other Embodiments

Embodiments of the present disclosure can also be realized by a computer of a system or apparatus that reads out and executes computer executable instructions recorded on a storage medium (e.g., non-transitory computer-readable storage medium) to perform the functions of one or more of the above-described embodiment(s) of the present disclosure, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2016-047309, filed Mar. 10, 2016, which is hereby incorporated by reference herein in its entirety.

What is claimed is:

1. An ophthalmologic photographing apparatus comprising:
    a detection unit configured to detect information on movement of an eye to be examined;
    a determination unit configured to determine, using the detected information, whether or not an imaging area for imaging the eye to be examined is beyond an edge of a predetermined range;
    a scanning unit configured to scan the eye to be examined with scanning light;
    a control unit configured to perform a tracking of the imaging area by controlling the scanning unit, using the detected information; and
    a selection unit configured to select one of a plurality of modes including (a) a first mode to perform the tracking in a case where the imaging area is determined not to be beyond the edge of the predetermined range, and not to perform the tracking in a case where the imaging area is determined to be beyond the edge of the predetermined range, and (b) a second mode to perform the tracking without making the determination by the determination unit.

2. The ophthalmologic photographing apparatus according to claim 1, wherein
    an OCT optical system for capturing a tomographic image of the eye to be examined, and an optical system for capturing a front image of the eye to be examined are configured as partially shared optical systems,
    the detection unit detects the information on the movement using the front image,
    the imaging area is an imaging area of the tomographic image, and
    the tracking of the imaging area is performed by controlling the scanning unit of the OCT optical system, using the detected information.

3. The ophthalmologic photographing apparatus according to claim 1, wherein, in a case where the second mode is selected, the tracking is allowed up to a range where imaging of the eye to be examined is guaranteed, the range corresponding to optical properties of the OCT optical system.

4. The ophthalmologic photographing apparatus according to claim 1, further comprising:
    a change unit configured to change a range where the imaging area is trackable; and
    a display control unit configured to display, on a display unit, a notification of the change of the range.

5. The ophthalmologic photographing apparatus according to claim 1, further comprising:
    a change unit configured to change a range where the imaging area is trackable; and
    a display control unit configured to display, on a display unit, a notification of the necessity or unnecessity of the change of the range, wherein the change unit changes the range at an instruction to change the range.

6. The ophthalmologic photographing apparatus according to claim 1, further comprising:
an acquiring unit configured to acquire a front image of the eye to be examined;
a display control unit configured to display the front image on a display unit;
a specification unit configured to specify the imaging area for imaging the eye to be examined on the displayed front image; and
a change unit configured to change a range where the imaging area is specifiable.

7. The ophthalmologic photographing apparatus according to claim 1, further comprising a change unit configured to change a range where the imaging area is trackable, wherein the change unit changes the range such that the range for follow-up imaging of the eye to be examined to a larger range than the range for imaging different from the follow-up imaging.

8. The ophthalmologic photographing apparatus according to claim 1, further comprising a change unit configured to change a range where the imaging area is trackable, wherein the change unit limits the range in a case where follow-up imaging of the eye to be examined is not performed, and changes the range in such a manner as not to limit the range in a case where the follow-up imaging is performed.

9. The ophthalmologic photographing apparatus according to claim 8, wherein a range to limit the range is a range where imaging of the eye to be examined is guaranteed.

10. The ophthalmologic photographing apparatus according to claim 1, further comprising:
a change unit configured to change a range where the imaging area is trackable; and
a scanning unit configured to scan the eye to be examined with measurement light, wherein
the change unit changes the range, using at least one piece of information on a scan pattern of the scanning unit and an imaging range.

11. The ophthalmologic photographing apparatus according to claim 1, further comprising a change unit configured to change a range where the imaging area is trackable, wherein the change unit changes the range, using at least one of information on a fixation state of the eye to be examined, information on a size of the imaging area, and information on a distance between the imaging area and the range.

12. The ophthalmologic photographing apparatus according to claim 1,
wherein the determination unit is configured (a) to determine, using the detected information, whether or not the imaging area is beyond an edge of a first range in a case where the first mode is selected, and (b) to determine, using the detected information, whether or not the imaging area is beyond an edge of a second range larger than the first range in a case where the second mode is selected.

13. The ophthalmologic photographing apparatus according to claim 1,
wherein the second mode is a follow-up imaging mode,
wherein the first mode is an imaging mode different from the follow-up imaging mode.

14. The ophthalmologic photographing apparatus according to claim 1,
wherein the tracking is performed without making the determination by the determination unit in a case where it is instructed to image the eye to be examined in the first mode.

15. A method for controlling an ophthalmologic photographing apparatus, comprising:
detecting information on movement of an eye to be examined;
determining, using the detected information, whether or not an imaging area for imaging the eye to be examined is beyond an edge of a predetermined range; and
performing a tracking of the imaging area by controlling a scanning unit configured to scan the eye to be examined with scanning light, using the detected information; and
receiving a selection of one of a plurality of modes including (a) a first mode to perform the tracking in a case where the imaging area is determined not to be beyond the edge of the predetermined range, and not to perform the tracking in a case where the imaging area is determined to be beyond the edge of the predetermined range, and (b) a second mode to perform the tracking without making the determination in the determination step.

16. The method for controlling an ophthalmologic photographing apparatus according to claim 15,
wherein (a) in a case where the first mode is selected, whether or not the imaging area is beyond an edge of a first range is determined, using the detected information, and (b) in a case where the second mode is selected, whether or not the imaging area is beyond an edge of a second range larger than the first range is determined, using the detected information.

17. A non-transitory computer-readable storage medium storing a program for causing a computer to execute steps in the method defined in claim 16.

18. A non-transitory computer-readable storage medium storing a program for causing a computer to execute steps in the method defined in claim 15.

19. An ophthalmologic photographing apparatus comprising:
a detection unit configured to detect information on movement of an eye to be examined;
a selection unit configured to select one of a plurality of imaging modes including a first mode and a second mode different from the first mode;
a scanning unit configured to scan the eye to be examined with scanning light;
a control unit configured to perform a tracking of an imaging area for imaging the eye to be examined by controlling the scanning unit, using the detected information;
a determination unit configured (a) to determine, using the detected information, whether or not the imaging area is beyond an edge of a first range in a case where the first mode is selected, and (b) to determine, using the detected information, whether or not the imaging area is beyond an edge of a second range larger than the first range in a case where the second mode is selected; and
a control unit configured (a) to perform first control of performing the tracking in a case where the imaging area is determined not to be beyond the edge of the first range, and not performing the tracking in a case where the imaging area is determined to be beyond the edge of the first range, and (b) to perform second control of performing the tracking in a case where the imaging area is determined not to be beyond the edge of the second range, and not performing the tracking in a case where the imaging area is determined to be beyond the edge of the second range.

20. A method for controlling an ophthalmologic photographing apparatus, comprising:
    detecting information on movement of an eye to be examined;
    receiving a selection of one of a plurality of imaging modes including a first mode and a second mode different from the first mode;
    performing a tracking of an imaging area for imaging the eye to be examined by controlling a scanning unit configured to scan the eye to be examined with scanning light, using the detected information;
    (a) determining, using the detected information, whether or not the imaging area is beyond an edge of a first range in a case where the first mode is selected, and (b) determining, using the detected information, whether or not the imaging area is beyond an edge of a second range larger than the first range in a case where the second mode is selected; and
    (a) performing first control of performing the tracking in a case where the imaging area is determined not to be beyond the edge of the first range, and not performing the tracking in a case where the imaging area is determined to be beyond the edge of the first range, and (b) performing second control of performing the tracking in a case where the imaging area is determined not to be beyond the edge of the second range, and not performing the tracking in a case where the imaging area is determined to be beyond the edge of the second range.

21. A non-transitory computer-readable storage medium storing a program for causing a computer to execute steps in the method defined in claim 20.

* * * * *